United States Patent
Weinstein et al.

[11] Patent Number: 5,538,505
[45] Date of Patent: Jul. 23, 1996

[54] HEMOSTASIS VALVE FOR CATHETER INTRODUCER HAVING THICKENED CENTRAL PARTITION SECTION

[75] Inventors: Lawrence A. Weinstein, Davie; Roberta D. Goode, Miami, both of Fla.

[73] Assignee: Cordis Corporation, Miami Lakes, Fla.

[21] Appl. No.: 229,595

[22] Filed: Apr. 19, 1994

Related U.S. Application Data

[63] Continuation-in-part of Ser. No. 77,242, Jun. 14, 1993, Pat. No. 5,350,363.

[51] Int. Cl.⁶ ............................................. A61M 5/178
[52] U.S. Cl. ......................... 604/167; 604/256; 251/149.1
[58] Field of Search .................................. 604/167, 256; 251/149.5

[56] References Cited

U.S. PATENT DOCUMENTS

| | | | |
|---|---|---|---|
| 4,424,833 | 1/1984 | Spector et al. | 137/849 |
| 4,610,674 | 9/1986 | Suzuki et al. | 604/282 |
| 4,626,245 | 12/1986 | Weinstein | 604/167 |
| 4,798,594 | 1/1989 | Hillstead | 604/167 |
| 4,895,565 | 1/1990 | Hillstead | 604/167 |
| 4,929,235 | 5/1990 | Merry et al. | 604/167 |
| 4,932,633 | 6/1990 | Johnson et al. | 251/149.1 |
| 5,102,395 | 4/1992 | Cheer | 604/167 |
| 5,114,408 | 5/1992 | Fleischhaker et al. | 604/167 |
| 5,167,637 | 12/1992 | Okada et al. | 604/167 |
| 5,176,652 | 1/1993 | Littrell | 604/167 |
| 5,211,633 | 5/1993 | Stouder | 604/167 |
| 5,242,413 | 9/1993 | Heiliger | 604/167 |
| 5,279,571 | 1/1994 | Larkin | 604/167 |
| 5,312,362 | 5/1994 | Pfolsgral et al. | 604/167 |
| 5,350,363 | 9/1994 | Goode et al. | 604/167 |

FOREIGN PATENT DOCUMENTS 0344907  12/1989  Japan .

OTHER PUBLICATIONS 2 sheets of drawings entitled hemaouet Plus Gasket.

*Primary Examiner*—John G. Weiss
*Attorney, Agent, or Firm*—Gerstman, Ellis & McMillin, Ltd.

[57] ABSTRACT

A hemostasis valve for a catheter such as a catheter sheath introducer comprises an elastomeric partition extending across an aperture in a hub carried by a catheter. The partition defines an annular, peripheral area which is secured to the hub. The partition further defines a second area positioned radially inwardly from the peripheral area. The second area is of substantially less thickness than the peripheral area. The partition further defines a central area positioned radially inwardly from the second area, the central area being of substantially greater thickness than the second area, and defining a slit therethrough to permit passage of the elongated member.

21 Claims, 1 Drawing Sheet

HEMOSTASIS VALVE FOR CATHETER INTRODUCER HAVING THICKENED CENTRAL PARTITION SECTION

CROSS-REFERENCE TO RELATED APPLICATION

This application is a continuation in part of Goode and Weinstein U.S. application Ser. No. 08/077,242, filed Jun. 14, 1993, now U.S. Pat. No. 5,350,363.

BACKGROUND OF THE INVENTION

Intravascular catheters such as angiographic or angioplasty catheters are introduced from the exterior of a patient into an artery or vein. After such an introduction, the catheter is advanced and maneuvered through the arteriovenous system to a desired site, which may be an area of arterial stenosis, or an area from which the x-ray contrast media is injected into the system. As described for example in Stevens U.S. Pat. No. 4,000,739, such a catheter may be emplaced by first inserting a hollow needle with a trocar through the skin into the lumen of the desired blood vessel. Following this, a guidewire is passed through the needle and advanced up the artery or vein toward the desired area. The needle can then be removed, leaving the guidewire in the vessel.

Following this, a catheter introducer comprising a tubular sheath and a removable, hollow stylet or dilator unit may be advanced together over the wire into the vessel. Then, the guidewire and the dilator unit may be removed, leaving only the sheath of the catheter introducer member present in the vessel. Then, desired catheters can be advanced through the sheath into the vessel, particularly an artery, while reliably maintaining a seal against blood loss as the catheter is advanced, and also between the times that a catheter is being advanced or maintained in the blood vessel.

The sheath of the catheter introducer carries a hub, which has partition-type hemostasis valve means on its proximal end, to avoid uncontrolled bleeding and air embolism. The dilator unit, and then respective catheters as desired, pass through this hemostasis valve. Specifically, hemostasis valves of the design disclosed in Hillstead U.S. Pat. Nos. 4,798,594 and 4,895,565, and Weinstein, U.S. Pat. No. 4,626,245, are known among numerous other designs. In the above designs, the elastomeric partition is carried by the hub, and defines a special slit which is particularly adapted to provide good sealing about an advancing catheter which passes through the catheter introducer. Improvements in the frictional resistance to catheter advancement are provided over a conventional, straight slit by the above.

In Goode and Weinstein copending application Ser. No. 08/077,242 cited above, a partition valve for a catheter hub on a catheter sheath introducer or the like is provided, in which the central portion of the partition which carries the slit is of reduced thickness compared with peripheral portions, which peripheral portions are used for securance of the partition within the hub. By this means and other improvements described therein, improvements in both sealing of a catheter extending through the hemostasis valve, and reduction of friction encountered by the catheter, are provided.

By this invention, yet further improvements are provided in a partition type hemostasis valve, having improved sealing capability coupled with reduced friction for a catheter or other elongated member which is passing through the partition valve. Thus, the valve of this invention provides improved utility and clinical benefits to catheter sheath introducers and the like. Additionally, tearing of the partition at the slit ends during catheter advancement or retraction can be further reduced in the partition valves of this invention, even without reinforcement of the slit ends.

DESCRIPTION OF THE INVENTION

By this invention a catheter is provided, being adapted to be introduced into a patient's blood vessel. Particularly, the catheter contemplated is a catheter sheath introducer, which of course is a catheter in its own right.

The catheter comprises a proximal hub which carries a hemostasis valve. A tubular sheath is connected to the hub to permit an elongated member such as a dilator unit or a catheter to extend through the hemostasis valve, the hub, and the sheath into a blood vessel.

The hemostasis valve of this invention comprises an elastomeric partition extending across an aperture in the hub. The partition defines an annular peripheral area which is secured to the hub, for example by an annular pressure seal. The partition further defines a second area, which is positioned radially inwardly from the peripheral area. The second area is of substantially less thickness than the peripheral area. For example, the average thickness of the second area may be about forty to eighty percent of the average thickness of the peripheral area.

The elastomeric partition further defines a central area which is positioned radially inwardly from the second area, and is integrally connected thereto. The central area is of substantially greater thickness than the second area. Preferably, the average thickness of the central area may be from about ten to fifty percent greater than the average thickness of the second area. Also, the central area defines a slit therethrough to permit passage of the elongated member through the partition and the entire catheter.

Preferably, the central area defines a lens-like shape, having a minimum peripheral thickness of essentially the thickness of the second area at its junction with the second area, and having greater thicknesses at central area portions which are spaced inwardly from the second area. Thus, the inner and outer surfaces of the central area are dome-like in shape.

The second area preferably comprises a circular ring of substantially constant thickness which surrounds the central area and is integral therewith. The second area is also integral with the peripheral area.

It is also preferable for the peripheral area to comprises a circular ring of substantially constant thickness surrounding the second area. As stated, the catheter hub can hold the partition with an annular pressure seal exerted against the peripheral area. The thickened, central area through which the slit extends provides improved sealing for catheters and the like projecting therethrough. At the same time, the relatively thinner second area results in a reduced frictional resistance for catheters which are advancing or retracting through the partition valve, coupled with the improved sealing characteristics.

It is preferred for the type of slit used to be that which is used in Hillstead U.S. Pat. Nos. 4,798,594, and 4,895,565, which are incorporated by reference herein. Briefly, the slit comprises intersecting radii at the beginning of the slit on one surface of the central area of the partition, which radii rotate through the thickness of the partition to define similar, intersecting radii on the other surface of the central portion, but typically at an angle to the first, intersecting radii.

Preferably, the intersecting radii are lines extending generally radially from an origin, with the lines occupying a circular area having a diameter of at least about 0.125 inch and no more than about 0.2 inch, typically no more than about 0.150 inch. Also, the maximum thickness of the central portion of the partition member is preferably of a thickness of 0.06 to 0.1 inch, while the thickness of the second area is preferably about 0.03 to 0.05 inch.

The thickness of the peripheral area is typically about equal to the maximum thickness of the central area.

Preferably, the elastomeric material used in the partition member and through which the slit is defined comprises a silicone rubber, although it is believed that other elastomers exhibiting equivalent properties may be used. Preferably, the slit-defining elastomeric material of the partition has an elongation to break of 900 to 1500 percent, as measured by the usual and conventional ASTM D412.

In the prior art slit partition hemostasis valves sold by the Cordis Corporation, a silicone rubber partition is used having a maximum elongation of about 750 percent as measured in similar manner. It has been found that the higher elongations used in this invention help to provide improved sealing characteristics over the prior art structures.

Also it is preferred for the elastomeric material to have a tensile strength of at least 11.5 megapascals, up to generally a practical maximum of about 15 megapascals, as measured by the same ASTM D412.

In the prior art slit partition valve sold by the Cordis Corporation and mentioned above, the tensile strength of the material of the elastomer partition is about 10.9 megapascals, which is of course significantly below the tensile strength of the elastomer materials used in this invention. This also contributes to the advantages of this invention as described above.

It is also preferred for the elastomeric material used herein to have a Shore A durometer of 45 to 70 as measured by ASTM D2240. The durometer of the prior Cordis slit partition hemostasis valve is about 40. These higher durometers used herein result in less frictional resistance exhibited by the valve.

Specifically, silicone elastomer materials which are preferred for use are available from the Dow Corning Corporation of Midland, Mich. under the name Silastic Q7-47-35, 50 or 65 medical grade ETR elastomer. The latter two digit numbers refer to the Shore A durometers of the materials.

The preferred tear strength of the elastomers used is at least 150 pounds/inch, as determined by ASTM D624, Die B. Preferably, the tear strength is at least 180 pounds/inch, with no critical maximum tear strength.

It is also preferred for at least one of the faces of the elastomeric partition, i.e. that face which rubs against the catheter or the like passing through it, to be coated with a silicone oil having a viscosity of 350 to 5000 cs. In the prior art Cordis product, Dow Corning 360 medical grade dimethylpolysiloxane oil was used, with the oil having a viscosity of 12,500 cs. It has been found that a reduction in frictional resistance can be achieved by reducing the viscosity of the silicone oil used to the above range, and applying it to the partition valve face. The silicone oil may comprise other silicones than dimethylpolysiloxane if desired, for example phenylmethylpolysiloxane copolymers with dimethylpolysiloxane, or polymers of copolymers having 3, 3, 3-trifluoropropylmethylsiloxane units.

Thus, by this invention, a partition valve is provided having significant distinctions from the valves of the prior art, and which are capable of exhibiting significant improvements in both sealing and friction reduction, with a substantially reduced risk of tearing of the valve during use.

DESCRIPTION OF SPECIFIC EMBODIMENTS

Figure 1:
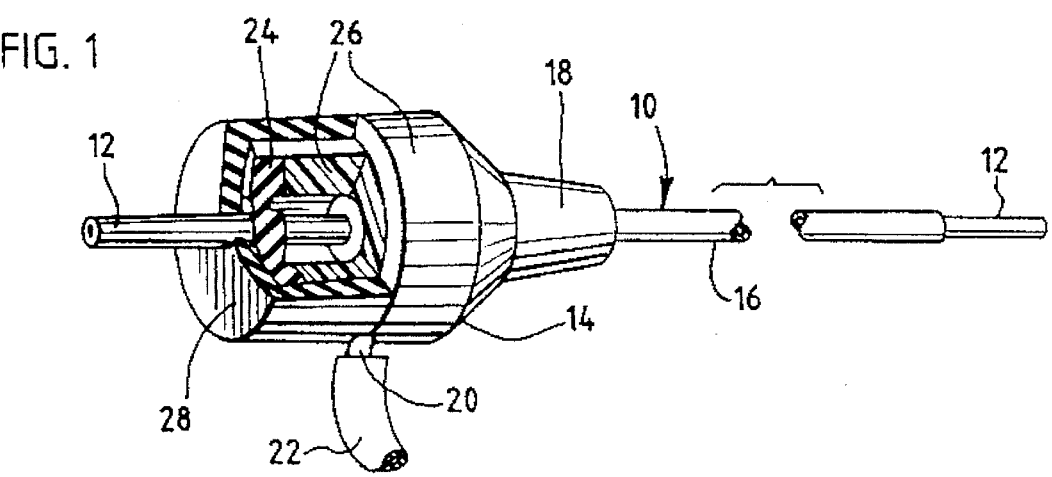
FIG. 1 is a perspective view, with a portion cut away, of a catheter introducer sheath which carries the hemostasis valve of this invention.

Referring to the drawings, FIG. 1 shows a catheter sheath introducer 10, adapted to receive an inner catheter 12 as shown for insertion into the vascular system of a patent. Catheter sheath introducer 10 is used to introduce a catheter into a blood vessel while preventing blood back flow along the outside surface of the catheter during procedures in which a catheter is inserted into the vessel. Thus, various catheters 12 may be inserted and removed from the blood vessel while catheter sheath introducer 10 stays in position. This greatly reduces the trauma to the blood vessel system.

Catheter sheath introducer 10 defines outer tubular housing 14, which carries cannular portion 16 of catheter sheath introducer 10, positioned in attached, telescoping, secured relation with tubular protrusion 18 of the housing.

Side port 20 may be of conventional design, being adapted for telescoping connection with plastic tubing 22, for providing a saline solution for flushing the interior of housing 14 and tubing extension 16.

Housing 14 carries a self-sealing, penetrable barrier, which is elastomeric partition valve member 24, made in accordance with this invention, preferably of silicone rubber as previously described. Apart from the new and improved design of partition valve member 24, the catheter sheath introducer of FIG. 1 may be identical to those of the prior art.

Figure 2:
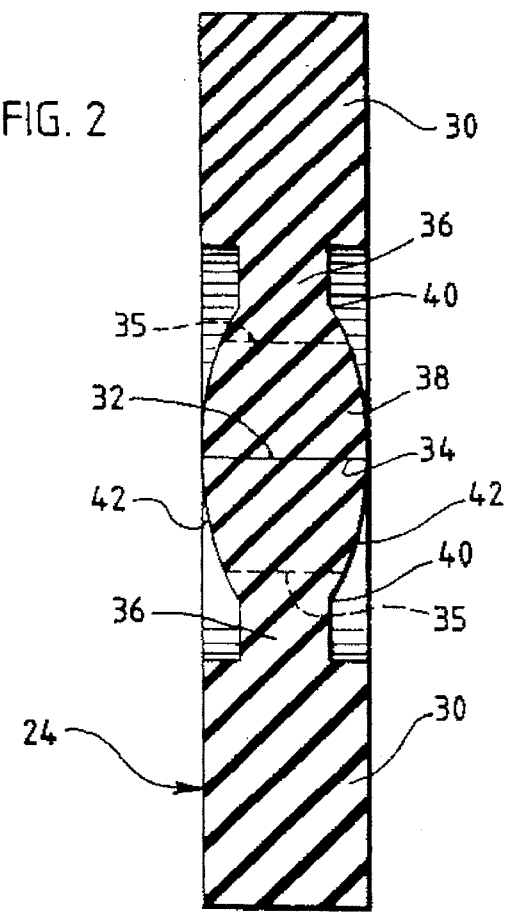
FIG. 2 is an enlarged, transverse, sectional view of the elastomeric partition member of FIG. 1.

Housing 14 may comprise casing portions 26, 28, which are sealed together in telescoping relation, and which peripherally capture elastomeric partition valve member 24 between them as shown. Partition 24 may be held with good sealing in those preferred cases as shown in which an annular peripheral portion 30 (FIG. 2) of partition 24 is thicker than other portions of the partition, and is gripped about its periphery by casing portions 26, 28.

Alternatively, casing portion 28 may be a screw cap, for adjustable, compressive retention of the periphery 30 of elastomeric barrier. Annular ribs may also be provided in each housing portion to provide more positive capture of the elastomeric portion 24.

Slit 32 is provided in partition 24, being preferably of a design as illustrated in Hillstead U.S. Pat. No. 4,798,594, comprising three to six intersecting radii 35 extending through partition 24 through each main surface of partition 24. The radii 35 rotate through the thickness of the partition, so that the intersecting radii on one surface of partition 24 are at an angle, typically 30° to 60°, to the corresponding radii 35 on the other surface of partition 24.

The respective radii are typically substantially equiangularly spaced, being spaced about an origin line 34 by about 120°. Alternatively, with four equiangularly spaced radii, the included angle between each radius may be 90°. Six spaced radii may define included angles of 60°. Two equiangularly spaced radii define and include an angle with each other of 180°, and thus define a single, straight line, for a simplified, helical version of the radial arrangement.

If desired, at least one of the faces of the elastomeric partition 24, i.e. that face which rubs against the catheter or the like passing through it, may be coated with a silicone oil having a viscosity of typically 350 to 500 cs., for a significant reduction in frictional resistance. The silicone oil may comprise dimethylpolysiloxane, or other commercially known siloxane polymers.

Positioned radially inwardly from annular peripheral area 30 as an integral part of partition 24, is a second, annular area 36 which is of substantially less thickness than peripheral area 30. Then, positioned radially inwardly from annular second area 36, is the lens shaped central area 38, which is also an integral part of partition 24. Central area 38 defines the slit 32, which preferably may have six equiangularly spaced, outwardly projecting radii 35 extending outwardly from origin line 34, helically rotating from one side of central area 38 to the other by an angle of about 30°.

It can be seen that central area 38 of lens-like shape has a minimum peripheral thickness at its point of junction 40 with annular second area 36, increasing in thickness in the radially inward direction in an arcuate manner to form domed faces 42. The point of maximum thickness coincides with origin line 34 from which the rotating radii 35 extend outwardly.

Both annular, peripheral area 30 and annular second area 36 can be seen to be of substantially constant thickness, with peripheral area 30 surrounding second area 36, and second area 36 surrounding central area 38.

The elastomeric material of partition 24 may be a silicone rubber as previously described having a durometer of 35, 50 or 65, for example, an elongation of 1200, a tensile strength of about 12 megapascals, and a tear strength of about 200 pounds/inch.

By this invention, a partition valve is provided for a catheter sheath introducer or the like having significant distinctions from the valves of the prior art, and which are capable of both exhibiting significant improvements in both sealing and friction reduction, with a substantially reduced risk of tearing of the valve during use.

The above has been offered for illustrative purposes only, and is not intended to limit the scope of the invention of this application, which is defined in the claims below.

That which is claimed is:

1. A catheter adapted to be introduced into a patient's blood vessel, said catheter comprising a proximal hub carrying a hemostasis valve, and a tubular sheath connected to said hub to permit an elongated member to extend through said hemostasis valve, hub, and sheath into a blood vessel, said hemostasis valve comprising an elastomeric partition extending across an aperture in said hub, said partition defining an annular peripheral area which is secured to said hub, said partition further defining a second area positioned radially inwardly from said peripheral area, said second area being of substantially less thickness than said peripheral area, said partition further defining a central area positioned radially inwardly from said second area, said central area being of substantially greater thickness than said second area and defining a slit therethrough to permit passage of said elongated member, said central area having a maximum thickness that is substantially equal to the thickness of said annular peripheral area.

2. The catheter of claim 1 in which said central area defines a (lens like shape,) having a minimum peripheral thickness of essentially the thickness of the second area at its junction with said second area, and having greater thicknesses at central area portions which are spaced inwardly from said second area.

3. The catheter of claim 2 in which said second area comprises a circular ring of substantially constant thickness surrounding said central area.

4. The catheter of claim 1 in which the average thickness of said second area is no more than about 80 percent of the average thickness of said peripheral area.

5. The catheter of claim 1 in which said peripheral area comprises a circular ring of substantially constant thickness surrounding said second area.

6. The catheter of claim 1 in which said elastomeric partition comprises a slit-defining elastomeric material which has elongation of 900 to 1500 percent.

7. The catheter of claim 6 in which the elastomeric material of said partition member has a tensile strength of at least 11.5 megapascals.

8. The catheter of claim 7 in which the elastomeric material of said partition member has a Shore 'A' durometer of 45 to 70.

9. The catheter of claim 8 in which the elastomeric material of said partition member is silicone rubber.

10. A catheter adapted to be introduced into a patient's blood vessel, said catheter comprising a proximal hub carrying a hemostasis valve, and a tubular sheath connected to said hub to permit an elongated member to extend through said hemostasis valve, hub, and sheath into a blood vessel, said hemostasis valve comprising an elastomeric partition extending across an aperture in said hub, said partition defining an annular, peripheral area which is secured to said hub, said partition further defining a second area positioned radially inwardly from said peripheral area, said second area being of substantially less thickness than said peripheral area, said partition further defining a central area positioned radially inwardly from said second area, said central area being of substantially greater thickness than said second area and defining a lens-like shape, said central area defining convex surfaces facing inwardly and outwardly, said central area having a maximum thickness that is substantially equal to the thickness of said annular, peripheral area, and said central area also defining a slit therethrough to permit passage of said elongated member.

11. The catheter of claim 10 in which said central area defines a minimum peripheral thickness of essentially the thickness of the second area at its junction with said second area, and having greater thicknesses as central area portions which are spaced inwardly from said second area.

12. The catheter of claim 11 in which said peripheral area comprises a circular ring of substantially constant thickness surrounding said second area.

13. The catheter of claim 12 in which said second area comprises a circular ring of substantially constant thickness surrounding said central area.

14. The catheter of claim 13 in which the average thickness of said second area is no more than about 80 percent of the thickness of said peripheral area.

15. The catheter of claim 14 in which said central area has a maximum thickness of about the thickness of said peripheral area.

16. The catheter of claim 10 in which the elastomeric material of said partition member has an elongation of 900 to 1500 percent and a tensile strength of at least 11.5 megapascals.

17. The catheter of claim 16 in which the elastomeric material of said partition member is a silicone rubber having a Shore 'A' durometer of 45 to 70.

18. The catheter of claim 10 in which said slit defines at each of said faces a plurality of 2 to 6 lines extending radially from an origin line, said lines occupying only the central area of said partition and rotating through said partition, whereby said radial lines on one side of the partition occupy an angle to the corresponding lines on the other side of the partition.

19. The catheter of claim 1 in which said slit defines at each of said faces a plurality of 2 to 6 lines extending radially from an origin line, said lines occupying only the central area of said partition and rotating through said partition, whereby said radial lines on one side of the partition occupy an angle to the corresponding lines on the other side of the partition.

20. A catheter adapted to be introduced into a patient's blood vessel, said catheter comprising a proximal hub carrying a hemostasis valve, and a tubular sheath connected to said hub to permit an elongated member to extend through said hemostasis valve, hub, and sheath into a blood vessel, said hemostasis valve comprising an elastomeric partition extending across an aperture in said hub, said partition defining a central area defining a slit extending therethrough, and a second area positioned radially outwardly from and substantially surrounding said central area, said second area being of substantially less average thickness than said central area, said partition being secured to said hub at a peripheral area thereof, said peripheral area having a thickness that is substantially equal to the thickness of said central area.

21. The catheter of claim 20 in which said central area defines a lens-like shape, said central area defining convex surfaces facing inwardly and outwardly, and having a minimum peripheral thickness of essentially the thickness of the second area at its junction with said second area, and having greater thickness at central area portions which are spaced inwardly from said second area.

* * * * *